United States Patent
Ishida et al.

(10) Patent No.: US 6,923,793 B2
(45) Date of Patent: Aug. 2, 2005

(54) CLAMP FOR WINGED NEEDLE

(75) Inventors: Masashi Ishida, Osaka (JP); Hiroyuki Nakagami, Osaka (JP)

(73) Assignee: Nipro Corporation, Osaka (JP)

( * ) Notice: Subject to any disclaimer, the term of this patent is extended or adjusted under 35 U.S.C. 154(b) by 170 days.

(21) Appl. No.: 09/870,583

(22) Filed: Jun. 1, 2001

(65) Prior Publication Data

US 2001/0049507 A1 Dec. 6, 2001

(30) Foreign Application Priority Data

Jun. 2, 2000 (JP) .......................... 2000-165761

(51) Int. Cl.$^7$ .............................................. A61M 5/00
(52) U.S. Cl. ...................................... 604/250; 604/246
(58) Field of Search ........................ 604/263, 171, 604/191, 198, 250, 174, 246; 128/919

(56) References Cited

U.S. PATENT DOCUMENTS

| | | | | |
|---|---|---|---|---|
| 4,802,650 A | * | 2/1989 | Stricker | 251/117 |
| 4,834,702 A | * | 5/1989 | Rocco | 604/43 |
| 5,035,399 A | * | 7/1991 | Rantanen-Lee | 251/10 |
| 5,053,017 A | * | 10/1991 | Chamuel | 604/192 |
| 5,318,546 A | * | 6/1994 | Bierman | 604/250 |
| 5,704,917 A | * | 1/1998 | Utterberg | 604/180 |
| 5,921,969 A | | 7/1999 | Vallelunga et al. | 604/263 |
| 5,968,016 A | | 10/1999 | Yerfino et al. | 604/177 |
| 6,139,532 A | * | 10/2000 | Howell et al. | 604/165.03 |
| 6,379,335 B1 | * | 4/2002 | Rigon et al. | 604/177 |
| 6,447,485 B2 | * | 9/2002 | Bierman | 604/174 |

FOREIGN PATENT DOCUMENTS

| | | |
|---|---|---|
| EP | 0 534 000 A2 | 3/1993 |
| JP | 2673682 | 7/1997 |
| JP | 2813886 | 8/1998 |
| WO | 99 12594 | 3/1999 |

* cited by examiner

Primary Examiner—Anhtuan T. Nguyen
Assistant Examiner—Jessica R. Baxter
(74) Attorney, Agent, or Firm—Kubovcik & Kubovcik

(57) ABSTRACT

A clamp for a winged needle that functions simultaneously as a protector and as a clamp and that does not require a recapping operation is provided. The clamp includes a flexible curved portion 1 including a tube insertion hole 11 provided on the proximal side and an upper member 2 and a lower member 3 connected via the curved portion 1 and which can be engaged on the distal sides thereof. The clamp is adapted to pressurize the tube 44 when the upper member 2 and the lower member 3 are engaged, and to generate a clearance through which at least a wing 4 can be introduced when the upper member 2 and the lower member 3 are not engaged. The upper member 2 or the lower member 3 is provided with a space 32 in which the needle 41 and the hub 42 can be stored.

1 Claim, 5 Drawing Sheets

CLAMP FOR WINGED NEEDLE

TECHNICAL FIELD OF THE INVENTION

The present invention relates to a clamp to be placed and used on a tube of a winged needle used mainly for hemodialysis.

BACKGROUND OF THE INVENTION

After a medical puncture needle is used, it is recapped for protecting the pointed tip of the needle. There is a recognized problem in that medical personnel are accidentally injured during this operation, which can result in infection with AIDS, hepatitis, and so on. Various measures have been taken to solve this problem so far, and for a winged needle, for example, technologies to dispose a protector slidably on the tube (see Japanese Patent Publication No. 2673682) or to connect a needle cannula supporting portion and a protector by a flexible connecting portion and bend the connecting portion to cover the protector on the needle cannula after use (see Japanese Patent Publication No. 2813886) have been developed.

On the other hand, in case of a winged needle to be used for hemodialysis, a clamp for temporarily blocking a flow path in a tube is disposed on the tube in order to prevent blood from blowing out at the time of connection of the blood circuit, for example.

Therefore, in the case of a winged needle to be used for hemodialysis, two members, that is, a protector and a clamp are necessary for preventing accidental pricking and blow-out of blood, which disadvantageously results in an increase in cost and complex operations for medical personnel.

The present invention is intended to solve the above-described problems, and the object of the present invention is to provide a member having a function as a protector and a function as a clamp, that is, a clamp for a winged needle with which is not necessary to perform a recapping operation.

SUMMARY OF THE INVENTION

After dedicated studies to achieve the above-described object, the inventors found that a clamp for winged needles having a function as a protector can be obtained by providing an upper member or a lower member of the clamp with a space for storing the needle and a hub to allow the needle and the hub to be introduced therein after use, and reached the present invention.

Therefore, the present invention is a clamp for a winged needle comprising a flexible curved portion on a proximal side having a tube insertion hole, an upper member and a lower member connected via the curved portion, the upper member and the lower member being capable of being detachably engaged at the distal ends thereof so that the tube is pressurized when the upper member and the lower member are engaged, and characterized in that a clearance through which at least the wing can be introduced is generated between the upper member and the lower member when not engaged, and a space for storing the needle and the hub is provided in the upper member or the lower member.

Preferably, a pair of left and right engaging hooks is provided on the upper member and an engaged portion that engages the engaging hooks is provided on the lower member.

DETAILED DESCRIPTION OF THE INVENTION

Figure 1:
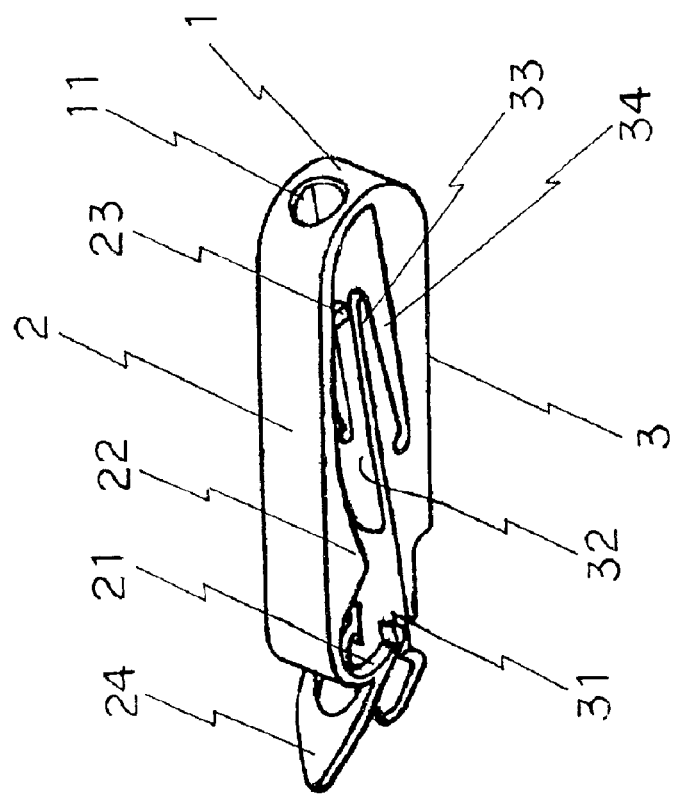
FIG. 1 is a perspective view showing an embodiment of the clamp for winged needles of the present invention.

An embodiment of the present invention is illustrated in the drawings. The winged needle comprises a needle cannula, a hub with a wing, and a tube.

FIG. 1 is a perspective view showing an embodiment of the present invention. The clamp for the winged needle of the present invention comprises a flexible curved portion 1 on the proximal side having a tube insertion hole 11, and an upper member 2 and a lower member 3 connected via the curved portion 1, so that the upper member 2 and the lower member 3 can be detachably engaged on the distal sides thereof. When the upper member 2 and the lower member 3 are engaged, the tube is pressurized, and when they are not engaged, a clearance through which at least the wing can be introduced is generated between the upper member 2 and the lower member 3. A space is provided for storing the needle and the hub on the upper member 2 or in the lower member 3.

The curved portion 1 is a flexible member for connecting the upper member 2 and the lower member 3. In this embodiment, the curved portion 1, the upper member 2, and the lower member 3 are formed integrally of a synthetic resin such as polystyrene, polycarbonate, polypropylene, polyethylene, or the like. The curved portion 1 comprises a tube insertion hole 11, and the clamp for a winged needle of the present invention is used with the tube inserted through the tube insertion hole 11. Though the extent of the curvature in this embodiment is such that the upper member 2 and the lower member 3 are situated more or less in parallel, the angle formed by these members may be as much as 30 degrees.

The upper member 2 is provided with a pair of left and right engaging hooks 21 on the distal end thereof, a pressurizing portion 22 for pressurizing, or squeezing, the tube on the proximal side from the engaging hooks 21, and a hub fixing means 23 for fixing the stored hub on the proximal side of the pressurizing portion 22.

The pair of left and right engaging hooks 21 is separated by a distance larger than the outer diameter of the tube so that the tube can be inserted there between, and are hooked at the tip so as to engage the engaged portion 31 formed on the lower member 3 described later. When the engaging hooks 21 and the engaged portion 31 are not engaged, a clearance through which at least the wing can be introduced is produced. The engaging hook 21 is inclined from the distal side toward the proximal side so that the wing of the winged needle can easily be introduced even when the clearance generated between the engaging hooks 21 and the engaged portion 31 is small as in this embodiment. It is also possible to provide a grip portion 24 on the engaging hooks 21 in order to facilitate the operation of releasing the engagement between the engaging hooks 21 and the engaged portion 31.

The pressurizing portion 22 is provided for pressurizing, or closing, the tube when the engaging hooks 21 and the engaged portion 31 are engaged, and is formed in a laterally extending angle in longitudinal cross section. The shape is not limited as far as the pressurizing portion can pressurize the tube. It is also possible to provide the engaging hooks 21 on the lower member 3 and the pressurizing portion 22 on the lower member 3 as long as the tube is not pressurized when the engaging hooks 21 and the engaged portion 31 are not engaged.

The hub fixing means 23 is a projection that comes into contact with the hub to prevent the stored needle from dropping out when the needle and the hub are stored in the storing space 32 on the lower member 3 described below and the engaging hooks 21 and the engaged portion 31 are engaged, and is recessed at the portion that comes into contact with the hub to as to mate with the shape of the cylindrical hub. Since the inner wall 26 (see FIG. 3) of the lower member 3 is gently inclined in a right upper direction in this embodiment, even when the hub fixing means 23 is formed into a small configuration, it can sufficiently fix the hub. When the lower member 3 is not inclined, the configuration of the hub fixing means 23 may be made larger without problem as long as the tube is not pressurized when the engaging hooks 21 and the engaged portion 31 are not engaged. The hub fixing means 23 may be omitted if there is no risk that the needle will drop out and injure a finger.

The lower member 3 is provided with the engaged portion 31 on the distal side thereof, and a storing space 32 on the proximal side from the engaged portion 31.

The engaged portion 31 is constructed of a pair of left and the right notches chipped away from both sides so as to engage with the engaging hooks 21 on the upper member 2. In addition to this configuration, a hole or the like can be employed.

The inner wall of the lower member 3 is formed with a shoulder 25 (see FIGS. 2 and 3), and the distal side of the inner wall 26 is relatively higher from the shoulder as a boundary. On the proximal side from the shoulder, there are provided a pair of sidewalls 33, and a space enclosed by these sidewalls 33 serves as an storing space 32 for the needle and the hub. When the wing is introduced deep inside the clamp for the winged needle, the needle and the hub drop into the storing space 32 to be stored. It is also possible to provide a slit 34 on the sidewalls 33 to make them flexible so that the wing can easily be introduced.

The distal ends of the upper member 2 and the lower member 3 are rounded so that the wing can easily be introduced.

In the winged needle of the present invention, it is also possible to provide a mechanism that makes the upper member 2 and lower member 3 unreleasable once engaged with the needle and hub stored.

The usage of the clamp for the winged needle shown in FIG. 1 will now be described with reference to FIG. 2 to FIG. 5.

Figure 2:
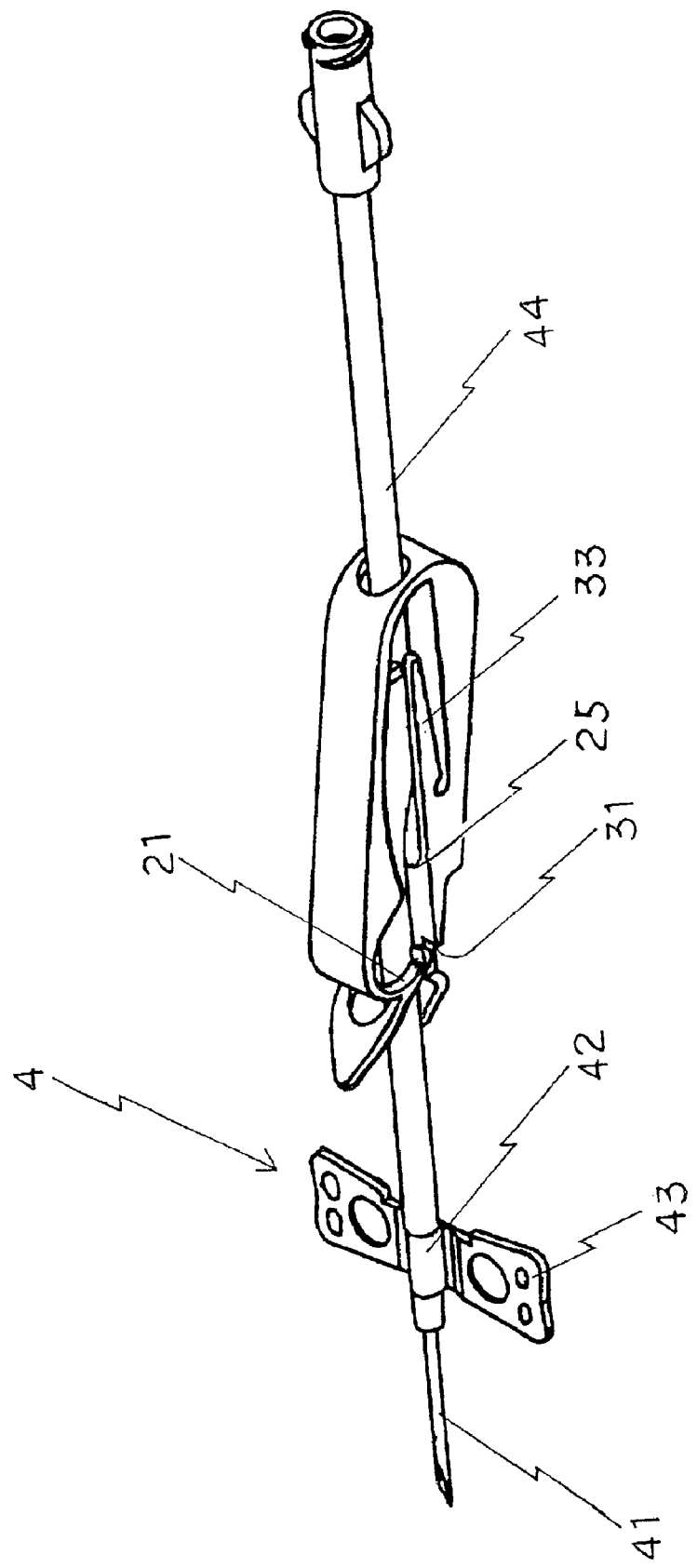
FIG. 2 is an explanatory drawing showing a state in which the clamp for winged needles shown in FIG. 1 is disposed on the tube of the winged needle.

As shown in FIG. 2, the clamp for the winged needle of the present invention is disposed on the tube 44 of the winged needle 4 in a state in which the engaging hooks 21 and the engaged portion 31 are not engaged.

Figure 3:
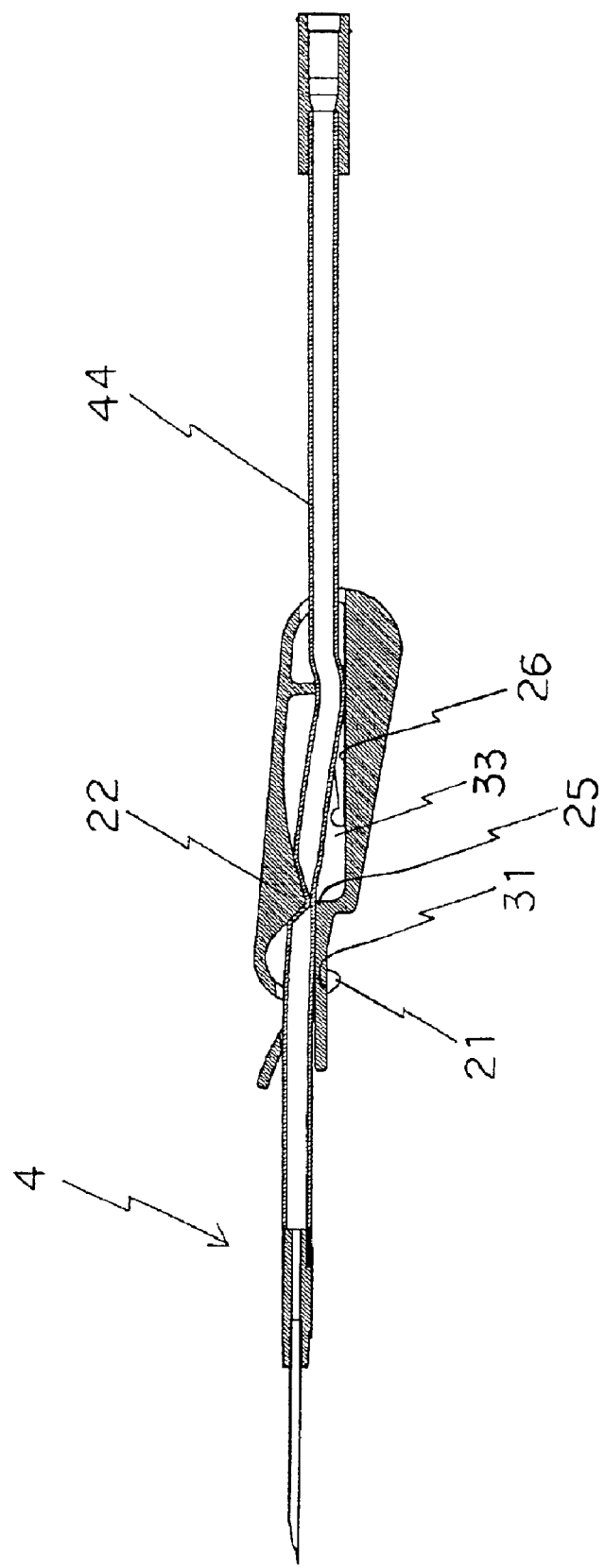
FIG. 3 is a longitudinal cross section of the clamp for winged needles shown in FIG. 2 showing a state of pressurizing the tube of the winged needle.

Initially, the needle 41 of the winged needle 4 is pricked into the tissue of a human's skin so that the tube 44 is filled with blood, and then the engaging hooks 21 and the engaged portion 31 of the clamp for the winged needle are engaged as shown in FIG. 3. At this time, the tube 44 is pressurized by the pressurizing portion 22 and blocked.

Then, the blood circuit (not shown) is connected to the tube 44, and consequently, the engagement between the engaging hooks 21 and the engaged portion 31 is released to carry out hemodialysis.

When hemodialysis is completed, the needle 41 is withdrawn from the tissue of the human's skin and the blood circuit is removed from the tube 44.

Figure 4:
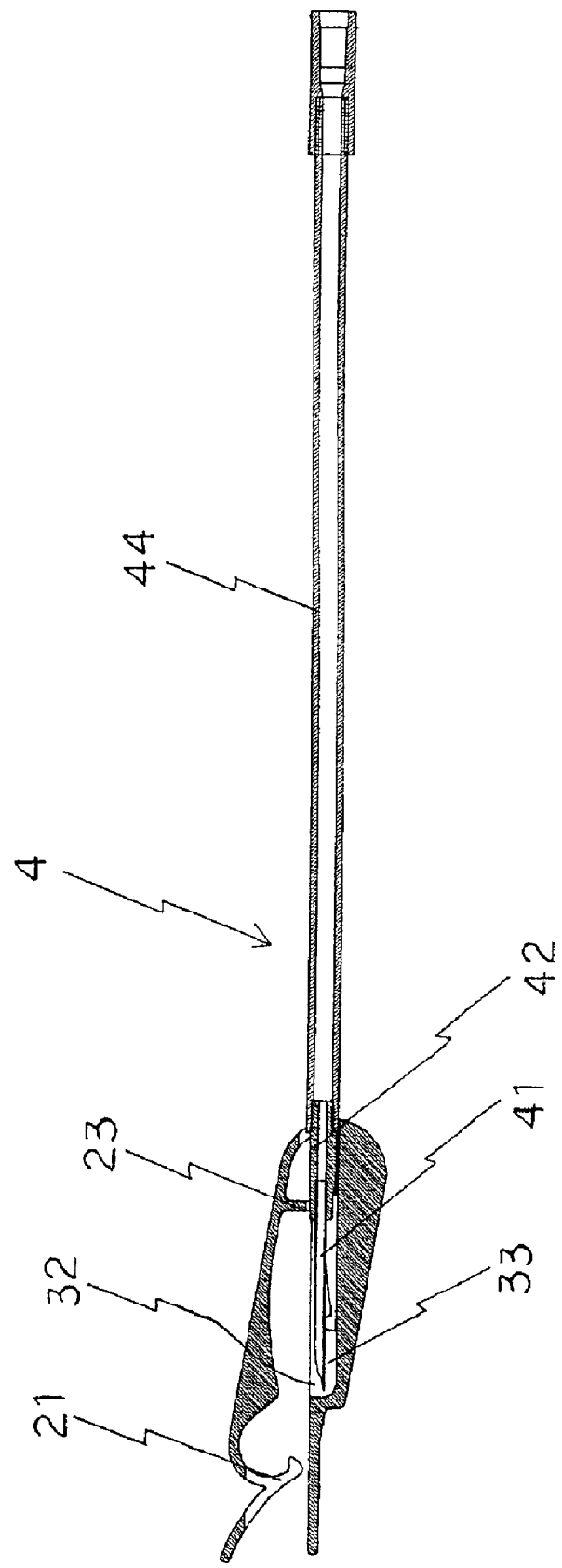
FIG. 4 is a longitudinal cross section of the clamp for winged needles shown in FIG. 2 showing a state of being slid to the position where the needle of the winged needle is stored.
Figure 5:
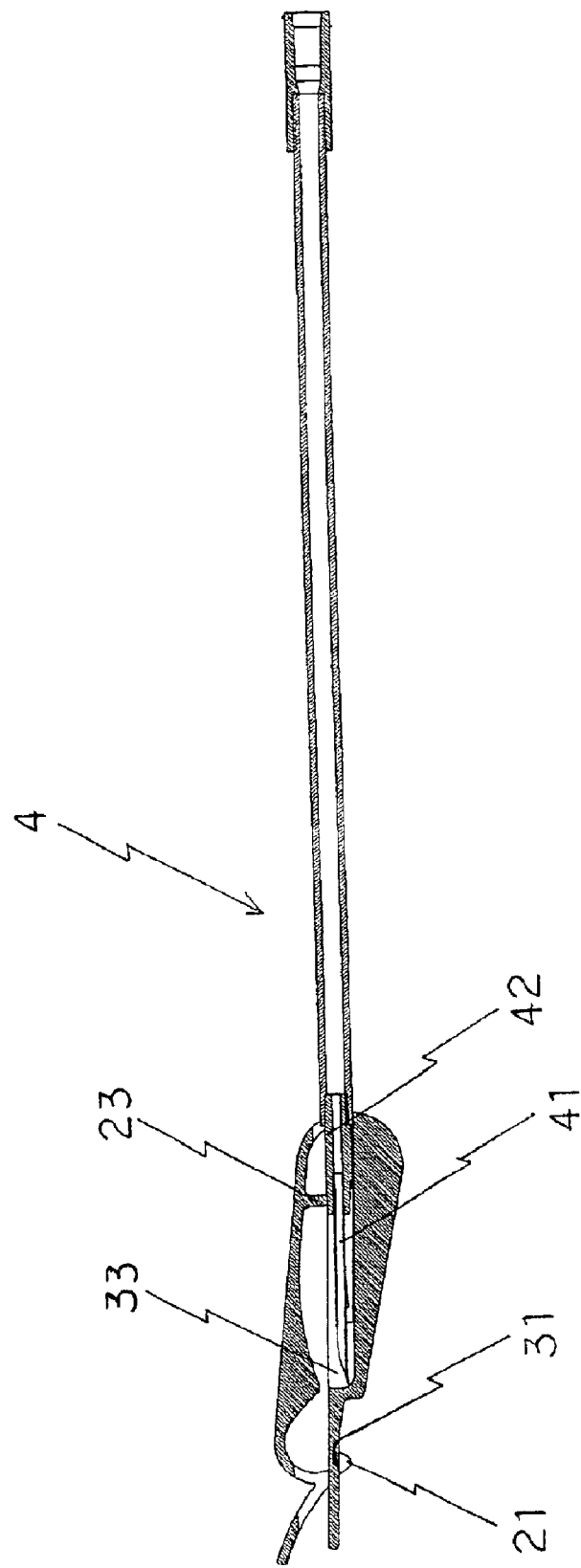
FIG. 5 is a longitudinal cross section showing a state in which the hub of the winged needle is fixed by the clamp for winged needles shown in FIG. 4.

As a last procedure, as shown in FIG. 4, the wing 43 of the winged needle 4 is introduced into the clamp for the winged needle and slid to the position where the needle 41 and the hub 42 are stored in the storing space 32, and then the engaging hooks 21 and the engaged portion 31 are engaged as shown in FIG. 5. At this moment, the hub 42 is fixed by the hub fixing means 23.

As described above, according to the present invention, the function as a protector and the function as a clamp can be provided simultaneously by a single member, the construction can be simplified and thus the workload of medical personnel is lightened.

What is claimed is:

1. A clamp to be placed and used on the tube of a winged needle and for storing the needle after use, the winged needle including a needle cannula, a hub with a wing, and a tube connected to the hub, said clamp having a proximal side and a distal side and comprising:

a flexible curved portion on the proximal side having a tube insertion hole;

an upper member and lower member connected via said curved portion, the upper member and the lower member being detachably engaged at distal ends thereof so that a clearance is provided between the upper member and the lower member when said members are not engaged through which said hub with a wing of said winged needle is introduced when the clamp is disposed on said tube and said hub with a wing is slid into the clamp;

a pressurizing portion provided on said upper member or lower member for engaging and pressurizing said tube when said members are engaged; and a space for storing said needle cannula and said hub provided in the upper member or lower member;

wherein the upper member is provided with a pair of left and right engaging hooks at its distal end, and the lower member is provided with notches or holes for engaging said engaging hooks.

* * * * *